(12) United States Patent
Zhuang

(10) Patent No.: US 11,020,048 B2
(45) Date of Patent: Jun. 1, 2021

(54) METHOD AND DEVICE FOR DETECTING SLEEP APNEA

(71) Applicant: BMC MEDICAL CO., LTD., Beijing (CN)

(72) Inventor: Zhi Zhuang, Beijing (CN)

(73) Assignee: BMC Medical Co., Ltd., Beijing (CN)

( * ) Notice: Subject to any disclaimer, the term of this patent is extended or adjusted under 35 U.S.C. 154(b) by 741 days.

(21) Appl. No.: 15/560,339

(22) PCT Filed: Dec. 31, 2015

(86) PCT No.: PCT/CN2015/100053
§ 371 (c)(1),
(2) Date: May 10, 2018

(87) PCT Pub. No.: WO2016/150227
PCT Pub. Date: Sep. 29, 2016

(65) Prior Publication Data
US 2018/0242903 A1 Aug. 30, 2018

(30) Foreign Application Priority Data
Mar. 23, 2015 (CN) .......................... 201510128945.6

(51) Int. Cl.
*A61B 5/00* (2006.01)
*A61B 5/08* (2006.01)
(Continued)

(52) U.S. Cl.
CPC .......... *A61B 5/4818* (2013.01); *A61B 5/0826* (2013.01); *A61B 5/09* (2013.01);
(Continued)

(58) Field of Classification Search
CPC .. A61B 5/4818; A61B 5/0826; A61M 16/026; A61M 16/0003; A61M 16/0006; A61M 16/022; A61M 16/025
See application file for complete search history.

(56) References Cited

U.S. PATENT DOCUMENTS

| 5,740,795 A | 4/1998 | Brydon |
| 6,675,797 B1 * | 1/2004 | Berthon-Jones ....... A61B 5/087 128/204.18 |

(Continued)

FOREIGN PATENT DOCUMENTS

| AU | 55383/98 A | 4/1998 |
| AU | 5538398 A | 4/1998 |

(Continued)

*Primary Examiner* — Margaret M Luarca
(74) *Attorney, Agent, or Firm* — Volpe Koenig

(57) ABSTRACT

The present invention provides a method and device for detecting sleep apnea, which overcomes the current defect that it is hard to distinguish the type of sleep apnea. The method comprises: monitoring an instantaneous output power and an instantaneous rotation speed of a motor for delivering air in a breathing device (S110); according to the instantaneous output power and the instantaneous rotation speed of the motor, obtaining an airway flow reference value represented for the air in an upper airway of a user using the breathing device (S120); when it is determined that the user currently has no spontaneous breathing according to the airway flow reference value, and corresponding duration has reached a preset time threshold value, determining the user to be in an apnea state (S130); judging whether the upper airway of the user is clear (S140); and determining the apnea of the user to be central apnea (S150) or obstructive apnea (S170) depending on whether the upper airway of the user is clear. The method and device can accurately and effectively distinguish the type of sleep apnea.

4 Claims, 2 Drawing Sheets

(51) Int. Cl.
*A61M 16/00* (2006.01)
*A61B 5/09* (2006.01)
*A61B 7/00* (2006.01)

(52) U.S. Cl.
CPC .......... *A61M 16/026* (2017.08); *A61B 7/003* (2013.01); *A61M 2016/0027* (2013.01)

(56) References Cited

U.S. PATENT DOCUMENTS

| | | |
|---|---|---|
| 2002/0077856 A1 | 6/2002 | Pawlikowski et al. |
| 2003/0121519 A1 | 7/2003 | Estes et al. |
| 2007/0227539 A1 | 10/2007 | Schwaibold et al. |
| 2008/0142011 A1* | 6/2008 | Aylsworth .......... A61M 16/026 128/204.23 |
| 2010/0319697 A1* | 12/2010 | Farrugia .............. F04D 27/001 128/204.18 |
| 2013/0324877 A1 | 12/2013 | Nonaka et al. |

FOREIGN PATENT DOCUMENTS

| | | |
|---|---|---|
| CN | 101060878 A | 10/2007 |
| CN | 103429290 A | 12/2013 |
| CN | 103445781 A | 12/2013 |
| CN | 103687540 A | 3/2014 |
| CN | 104302338 A | 1/2015 |
| WO | 2006/047826 A1 | 5/2006 |
| WO | 2010/054481 A1 | 5/2010 |
| WO | 2012/127358 A1 | 9/2012 |
| WO | 2013/152403 A1 | 10/2013 |

* cited by examiner

METHOD AND DEVICE FOR DETECTING SLEEP APNEA

CROSS REFERENCE TO RELATED APPLICATIONS

The present application claims the priority of PCT Application PCT/CN2015/100053, entitled "Method and Device for Detecting Sleep Apnea" filed Dec. 31, 2015, which claims the priority of Chinese Patent Application CN201510128945.6, entitled "Method and Device for Detecting Sleep Apnea" filed Mar. 23, 2015, the entire disclosure of which is incorporated herein by reference.

FIELD OF THE INVENTION

The present invention relates to a technique for detecting apnea during sleep, and more particularly relates to a method and device for detecting sleep apnea.

BACKGROUND OF THE INVENTION

Sleep apnea hypopnea syndrome (SAHS) refers to a sleep breathing diseases characterized by more than 30 episodes of paused breathing during sleep of 7 hours per night or an Apnea-Hypopnea Index (AHI) being greater than or equal to 5 times per hour, accompanied with clinical symptoms such as hypersomnia.

The sleep apnea is commonly categorized in three types: obstructive sleep apnea (OSA), central sleep apnea (CSA), and mixed sleep apnea (MSA).

Among them, OSA refers to symptoms of breathing pause and hypoventilation caused by collapse of the upper airway during sleep, in which case the oral and nasal air flow stops while the thoracoabdominal breathing movement still exits. CSA refers to symptoms that airway is not blocked but breathing pause exits, caused by respiratory center dysfunction of the central nervous system, or the lesion of nerves of dominated respiratory muscle or respiratory muscle, in which case both the oral and nasal air flow and thoracoabdominal breathing movement stop. MSA is the combination of CSA and OSA.

At present, continuous positive airway pressure (CPAP) machine is widely used in treatment for SAHS among those non-surgical treatment measures. The basic principle of treatment of CPAP machine is to apply mild air pressure on a continuous basis to the patient's upper airway, in order to relieve or alleviate the apnea and hypopnea symptoms.

Through research, the inventors have found that CPAP machine is more effective in the treatment of OSA. However, CSA cannot be effectively treated by CPAP machine due to its cause of disease. In addition, it is hard for CPAP machine to effectively distinguish CSA from OSA.

Since in the prior art it is hard to distinguish the type of sleep apnea, i.e., CSA and OSA, it is impossible to apply specific treatment according to the particular type of sleep apnea.

SUMMARY OF THE INVENTION

The technical problem to be solved by the present invention is to overcome the defect in the prior art that it is hard to distinguish the type of sleep apnea, and thus it is impossible to apply specific treatment according to the particular type of sleep apnea.

To solve the abovementioned technical problem, the embodiments of the present application provide a method for detecting sleep apnea, the method comprises: monitoring an instantaneous output power and an instantaneous rotation speed of a motor delivering air in a breathing device; according to the instantaneous output power and the instantaneous rotation speed of the motor, obtaining an airway flow reference value represented for the air in an upper airway of a user using the breathing device; when it is determined that the user currently has no spontaneous breathing according to the airway flow reference value, and the duration has reached a preset time threshold value, determining the user to be in an apnea state; judging whether the upper airway of the user is clear; and determining the apnea of the user to be central apnea or obstructive apnea depending on whether the upper airway of the user is clear.

Preferably, the airway flow reference value is obtained according to an equation as follows:

$$F = \frac{P*N}{K_1},$$

where F is the airway flow reference value, P is the instantaneous output power of the motor, N is the instantaneous rotation speed of the motor, and $K_1$ is a constant.

Preferably, the step of judging whether the upper airway of the user is clear comprises: superimposing oscillating pressure wave based on the treatment pressure currently supplied by the breathing device to obtain a change amount in flow and pressure after the oscillating pressure wave is superimposed; determining that the upper airway of the user is blocked when the change amount in flow and pressure exceeds a preset change threshold, otherwise, determining that the upper airway of the user is clear.

Preferably, after the oscillating pressure wave is superimposed, the change amount in flow and pressure is obtained according to an equation as follows:

$$M = \left(\frac{1}{n}\sum_{i=1}^{n} V_i\right) * \left(\frac{1}{n}\sum_{i=1}^{n} p_i\right) \bigg/ K_2,$$

where M is the change amount in flow and pressure, n is a number of cycles of the oscillating pressure wave superimposed on the treatment pressure, $V_i$ is a total change amount of the airway flow reference value in each cycle of the oscillating pressure wave, $p_i$ is a total change amount of an output pressure in each cycle of the oscillating pressure wave, and $K_2$ is a constant.

Preferably, $V_i$ is obtained according to an equation as follows: $V_i = \sum_{i=1}^{n}(F-F_i)$, where F is the airway flow reference value, and $F_i$ is a minimum value of the airway flow reference value F in each cycle.

Preferably, $p_i$ is obtained according to an equation as follows: $p_i = \sum_{i=1}^{n}(p-p_{avg})$, where p is the output power, $p_{avg}$ is an average of p for a period of time before the oscillating pressure wave is superimposed.

Preferably, after it is determined that the apnea of the user is obstructive apnea, adjusting the treatment pressure of the air provided by the breathing device.

The embodiments of the present application further provide a device for detecting sleep apnea, the device comprises: a monitoring device that monitors an instantaneous output power and an instantaneous rotation speed of a motor delivering air in a breathing device; a calculating unit for obtaining an airway flow reference value represented for the air in an upper airway of a user using the breathing device according to the instantaneous output power and the instantaneous rotation speed of the motor; a first determining unit for determining the user to be in an apnea state when it is determined that the user currently has no spontaneous breathing and corresponding duration has reached a preset time threshold value according to the airway flow reference value; a second determining unit for judging whether the upper airway of the user is clear; and an identifying unit for determining the apnea of the user to be central apnea or obstructive apnea depending on whether the upper airway of the user is clear.

Preferably, the calculating unit obtains the airway flow reference value according to an equation as follows:

$$F = \frac{P*N}{K_1},$$

where F is the airway flow reference value, P is the instantaneous output power of the motor, N is the instantaneous rotation speed of the motor, and $K_1$ is a constant.

Preferably, the second determining means is further configured to: superimpose an oscillating pressure wave based on the treatment pressure currently supplied by the breathing device to obtain the change amount in flow and pressure after the oscillating pressure wave is superimposed; and determines that the upper airway of the user is blocked when the change amount in flow and pressure exceeds a preset change threshold, otherwise, determines that the upper airway of the user is clear.

As compared with the prior art, the embodiments of the present application make it possible to accurately and effectively distinguish whether the sleep apnea is CSA type or OSA type, such that it enables to apply specific treatment to users according to the type of sleep apnea they experience in a more suitable and effective manner.

Other advantages, objects and features of the present invention will be to some extent set forth in the following description, and to some extent, based on a study of the below description the skilled person in the art will be apparent, or can get guidance from the practice of the invention. Objectives and other advantages of the present invention can be realized and attained through the structures particularly pointed out in the following description, claims, and drawings.

BRIEF DESCRIPTION OF DRAWINGS

The accompanying drawings which are intended to provide a further understanding of the invention and which form a part of the specification are intended to be illustrative of the invention in conjunction with the embodiments of the invention and are not to be construed as limiting the invention.

DETAILED DESCRIPTION OF THE EMBODIMENTS

Figure 1:
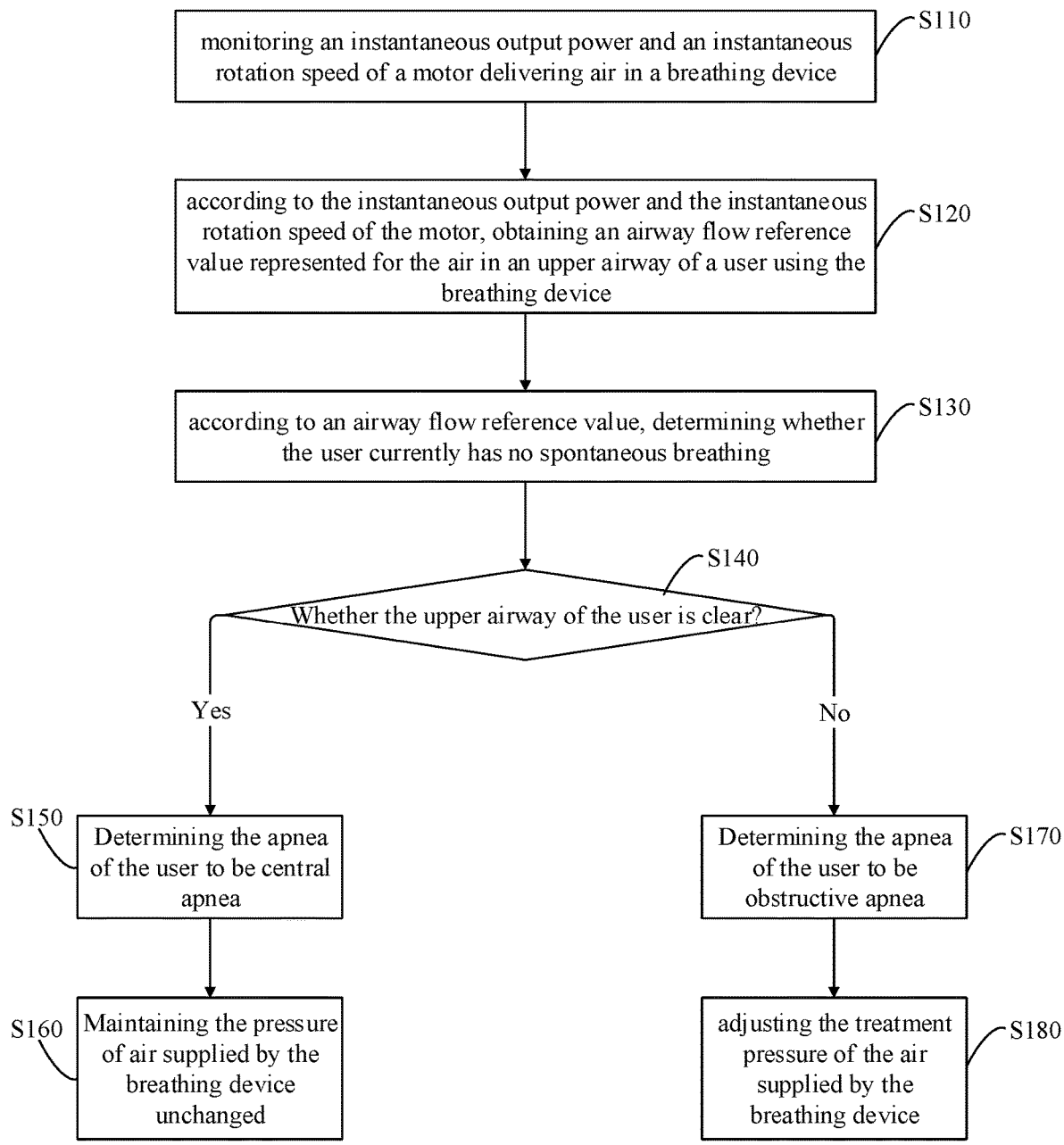
FIG. 1 is a flow chart illustrating an embodiment of the method for detecting sleep apnea according to the present application.

The present disclosure will be explained in detail with reference to the examples and the accompanying drawings, whereby it can be fully understood how to solve the technical problem by the technical means according to the present disclosure and achieve the technical effects thereof, and thus the technical solution according to the present disclosure can be implemented. It is important to note that as long as there is no structural conflict, all the technical features mentioned in all the examples may be combined together in any manner, and the technical solutions obtained in this manner all fall within the scope of the present disclosure.

Besides, the steps in the flowchart shown in the drawings can be executed in a computer system as a set of computer executable instructions. In addition, although the flowchart shows the logical order of these steps, in some cases, the steps shown or described herein may be carried out in different order.

An embodiment of the method for detecting sleep apnea according to the present application is able to detect whether sleep apnea happens to users using the breathing device for CPAP treatment.

As shown in FIG. 1, an embodiment of the method for detecting sleep apnea mainly comprises the following steps:

At step S110, monitoring an instantaneous output power and an instantaneous rotation speed of a motor delivering air in a breathing device providing CPAP treatment for the user.

At step S120, according to the instantaneous output power and the instantaneous rotation speed of the motor, obtaining an airway flow reference value represented for the air in an upper airway of a user using the breathing device. The embodiment of the present application is able to judge whether the user in the sleep state is experiencing apnea through detecting the air flow amount in the user's airway during sleep period.

At step S130, according to an airway flow reference value, determining whether the user currently has no spontaneous breathing. When the airway flow reference value is obviously smaller than the flow value during the normal breathing (for example, the magnitude of change in the airway flow reference value is smaller than 10% of the magnitude of change in the airway flow during normal breathing), it can be determined that the user already has no spontaneous breathing. If it is determined that the user is in the state having spontaneous breathing, the method continues monitoring the instantaneous output power and the instantaneous rotation speed of the motor.

At step S140, when the duration for which the user has no spontaneous breathing has reached or exceeded a preset time threshold value, determining the user to be in an apnea state. In this case, it is judged whether the upper airway of the user is clear. If clear, step S150 is proceeded; if not, step S170 is proceeded. The preset time threshold value may be, for example, 5 seconds.

If it is determined that the duration for which the user has no spontaneous breathing does not exceed the preset time threshold value, it is continued to monitor the instantaneous output power and the instantaneous rotation speed of the motor.

At step 150, if it is determined that the upper airway of the user is clear, it is explained that the upper airway of the user is not blocked, then it is considered that the apnea is caused by the reasons such as respiratory center dysfunction of the central nervous system, or the lesion of nerves of dominated respiratory muscle or respiratory muscle, thus the apnea is determined to be CSA. In this case, step S160 is proceeded.

At step S160, recording the CSA event, maintaining the pressure of air supplied by the breathing device unchanged and returning to step S110 to continue monitoring the instantaneous output power and the instantaneous rotation speed of the motor.

At step S170, if it is determined that the upper airway of the user is blocked, it is explained that the current apnea is caused by collapse of the upper airway, then determining the apnea to be OSA. In this case, step S180 is continued to proceed.

At step S180, according to clinical experience, if the upper airway of the user has the phenomenon of blocking, adjusting the treatment pressure of the air supplied by the breathing device. At this time, it is necessary to increase the pressure of the air supplied by the breathing device in order to treat the OSA.

In the embodiment of the present application, the airway flow reference value may be obtained from the instantaneous output power and the instantaneous rotation speed of the motor delivering air in the breathing device.

Through research, the inventors have found that when the user is using the breathing device for CPAP treatment during sleep, there is a corresponding relationship between the airway flow and the instantaneous output power and the instantaneous rotation speed of the motor delivering air in the breathing device. Therefore, an airway flow reference value for the air passing the breathing device may be obtained from the instantaneous output power and the instantaneous rotation speed of the motor in the breathing device.

In particular, the airway flow reference value may be obtained according to the following equation:

$$F = \frac{P*N}{K_1} \quad \text{Equation (1)}$$

where, F represents the airway flow reference value, P represents the instantaneous output power of the motor, N represents the instantaneous rotation speed of the motor, and $K_1$ is a constant which is derived from simulation in the embodiments of the present application. An active lung simulator ASL5000 is used for simulating the breathing of the patient. It is connected to the breathing machine to simulate the detection of patient's breathing by the breathing machine. Multiplying the airway flow reference value calculated from P and N by the constant $K_1$ makes the result fall into a proper range of numerical values and imposes the estimation of air flow in the airway with a proper accuracy. In some of the embodiments of the present application, the value of this constant $K_1$ may be 2000.

The airway flow reference value obtained through the above equation (1) may be subsequently used to determine whether the user is experiencing an apnea.

The above step S140 of determining whether the upper airway of the user is clear may be performed by superimposing an oscillating pressure wave of known frequency and amplitude based on the treatment pressure provided by the current breathing device. In some of the embodiments of the present application, this oscillating pressure wave of known frequency and amplitude may be a 1 Hz square wave, and the oscillation amplitude of which may vary with the current treatment pressure of the breathing device.

In the embodiment of the present application, the ASL5000 is used for simulating the breathing of the patient. It is connected to the breathing machine to simulate the detection of apnea events by the breaching machine. Under the fixed treatment pressure, oscillating pressure waves of different amplitudes are superimposed when the active lung simulator are experiencing OSA and CSA, and the waveforms of the airway flow reference value are recorded respectively. The waveforms of the airway flow reference value during the superimposing of the oscillating pressure waves of respective amplitudes are compared to select the amplitude that distinguishes the OSA and CSA in maximum. For example, for the treatment pressure of 4 cmH$_2$O, 7 cmH$_2$O, 11 cmH$_2$O and 15 cmH$_2$O, the optimal amplitude of the oscillating pressure wave is 0.3 cmH$_2$O, 0.3 cmH$_2$O, 0.35 cmH$_2$O and 0.4 cmH$_2$O, respectively. The corresponding optimal amplitude of the oscillating pressure wave may also be obtained for other treatment pressures of the breathing device.

By using the oscillating pressure wave having optimal amplitude, the embodiment of determining the status of the airway can have obvious distinction between OSA and CSA.

After starting from superimposing oscillating pressure wave on ½ cycle to the end of superimposing oscillating pressure, if the oscillating pressure of n cycles in total is superimposed (n is an positive integer equal to or greater than 1), then the change amount M in the flow and pressure may be obtained according to the following equation:

$$M = \left(\frac{1}{n}\sum_{i=1}^{n} V_i\right) * \left(\frac{1}{n}\sum_{i=1}^{n} p_i\right) / K_2 \quad \text{Equation (2)}$$

where, $V_i$ represents the total change in the airway flow reference value F during each cycle which takes the rising edge of one oscillating pressure value as the start of this cycle and the rising edge of a next oscillating pressure value as the end of this cycle and is obtained according to the following equation:

$$V_i = \Sigma_{i-1}{}^{n}(F-F_i) \quad \text{Equation (3)}$$

where, $p_i$ represents the total change in the output pressure (i.e., pressure of the air outputted from the breathing device) during each cycle which takes the rising edge of one oscillating pressure value as the start of this cycle and the rising edge of a next oscillating pressure value as the end of this cycle and is obtained according to the following equation:

$$p_i = \Sigma_{i-1}{}^{n}(p-p_{avg}) \quad \text{Equation (4)}$$

In the equation (3), $F_i$ represents the minimum value of the airway flow reference value F in each cycle.

In the equation (4), $p_{avg}$ represents the average of the output power p for a period of time (for example, 5 seconds) before the oscillating pressure wave is superimposed.

$K_2$ is a constant. In the embodiment of the present application, the active lung simulator ASL5000 is used for simulating the breathing of the patient. It is connected to the breathing machine to simulate the detection of apnea events by the breathing machine. Multiplying the obtained value M with a constant $K_2$ makes the value M fall into a proper range of numerical values and at the same time providing sufficient distinction between OSA and CSA. In some of the embodiments, the value of this constant may be 1000.

After calculating the change amount M of the flow and pressure, M is then compared with a preset change threshold $M_{Th}$.

If $M > M_{Th}$, it is determined that the upper airway of the user is blocked and that the apnea experienced by the user is OSA.

If $M<M_{Th}$, it is determined that the upper airway of the user is clear and that the apnea experienced by the user is CSA.

The inventors have used the active lung simulator ASL5000 for simulating the breathing of the patient and connected it to the breathing machine to simulate the detection of apnea events by the breaching machine. After simulating a certain number of OSA and CSA events and obtaining the values M, the change threshold $M_{Th}$ is determined according to these M values, so as to make the value M for the CSA and OSA fall into the corresponding interval, thus ensuring the distinction between OSA and CSA in maximum. Based on numerous experiments, it has been found that the preset change threshold $M_{Th}$ varies with the current treatment pressure of the breathing device. For example, regarding the treatment pressure of 4 $cmH_2O$, 7 $cmH_2O$, 11 $cmH_2O$ and 15 $cmH_2O$, the change threshold $M_{Th}$ may be optimally preset to 10, 100, 200 and 200, respectively. Under other treatment pressures, appropriate threshold values may also be determined through experiments.

For a user in sleep state, the amplitude of change in airway flow is very small. Therefore, it is hard to detect the change in airway flow of the user in sleep mode with flow sensor. The embodiments of the present application obtain the airway flow and its change according to the instantaneous rotation speed of the motor in the breathing device without requiring a specific flow sensor to detect airflow and its change, thereby enhancing the accuracy, stability and efficiency of airway flow detection. Moreover, in contrast to detecting the air flow change using the flow sensor, the embodiments of the present application does not need flow sensor, thereby reducing the hardware cost of breathing device and avoiding the situation where the accuracy of airway flow and apnea detection is dependent on performance of the flow sensor.

It shall be noted that some constants and/or thresholds used in the embodiments of the present application are acquired based on numerous experiments. In practice, they may be slightly adjusted according to actual needs. These constants or thresholds are not particularly limited in the present application. Any technical solutions embodying the concept of present application fall into the scope of the present application, even if the constants and/or thresholds used in these solutions are not completely identical with those used in the embodiments of the present application. These constants and/or thresholds include but not limited to the constant $K_1$, constant $K_2$, change threshold $M_{TH}$, and time threshold etc.

Figure 2:
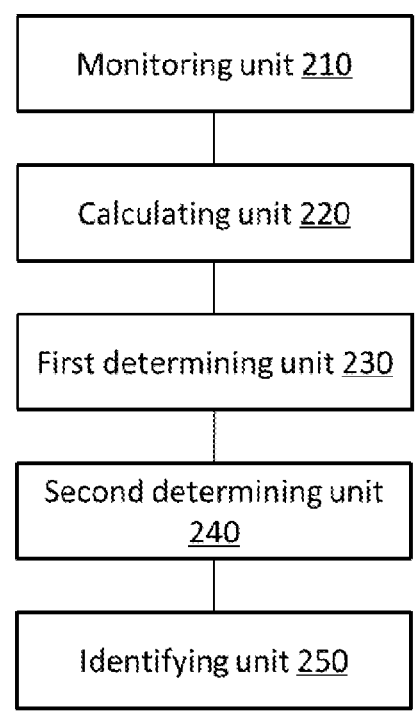
FIG. 2 is a schematic view of the structure of an embodiment of the device for detecting sleep apnea according to the present application.

An embodiment of the device for detecting sleep apnea according to the present application is able to detect whether sleep apnea happens to users using the breathing device for CPAP treatment. As shown in FIG. 2, the embodiment of the detecting device mainly includes a monitoring unit 210, a calculating unit 220, a first determining unit 230, a second determining unit 240, and an identifying unit 250.

The monitoring unit 210 is for monitoring the instantaneous output power and the instantaneous rotation speed of a motor for delivering air in the breathing device.

The calculating 220, connected to the monitoring means 210, is for obtaining an airway flow reference value represented for the air in an upper airway of a user using the breathing device according to the instantaneous output power and the instantaneous rotation speed of the motor monitored by the monitoring unit 210.

The first determining means 230, connected to the calculating unit 220, is for determining that the user is in an apnea state when it is determined that the user currently has no spontaneously breathing according to the airway flow reference value, and the duration has reached a preset time threshold value.

The second determining unit 240, connected to the first determining unit 230, is for determining whether the upper airway of the user is clear when the first determining unit 230 determines that the user is in the apnea state.

The identifying unit 250, connected to the second determining unit 240, is for determining that the apnea of the user is central apnea or obstructive apnea depending on whether the upper airway of the user is clear.

In the embodiment of the present application, the calculating unit 220 may obtain the airway flow reference value according to the above mentioned Equation (1).

In the embodiment of the present application, the second determining unit 240 is further used to: superimpose an oscillating pressure wave on the basis of the treatment pressure currently supplied by the breathing device to obtain the change amount in flow and pressure after the oscillating pressure wave is superimposed; when the change amount in flow and pressure exceeds the preset change threshold, determine that the upper airway of the user is blocked, otherwise, the upper airway of the user is clear.

Regarding the embodiment of the device for detecting the sleep apnea, reference may be made to the above described embodiment of the method for detecting the sleep apnea.

Those skilled in the art understand that each module or each step of the present document can be implemented by a universal computing device, and they can be integrated in a single computing device, or distributed in a network made up by a plurality of computing devices. Alternatively, they can be implemented by program codes executable by the computing device. Thus, they can be stored in the storage device and implemented by the computing device, or they are made into each integrated circuit module respectively, or a plurality of modules or steps therein are made into a single integrated circuit module to be implemented. In this way, the present application is not limit to any specific form of the combination of the hardware and software.

The above embodiments are described only for better understanding, rather than restricting, the present disclosure. Any person skilled in the art can make amendments to the implementing forms or details without departing from the spirit and scope of the present disclosure. The scope of the present disclosure should still be subjected to the scope defined in the claims.

The invention claimed is:

1. A method for detecting sleep apnea of a user using a breathing device having a motor for delivering air, the method comprising:
    monitoring an instantaneous output power and an instantaneous rotation speed of the motor for delivering air in the breathing device;
    according to the instantaneous output power and the instantaneous rotation speed of the motor, obtaining an airway flow reference value representing a flow of air in an upper airway of the user;
    when it is determined that the user currently has no spontaneous breathing according to the airway flow reference value, and a corresponding duration has reached a preset time threshold value, determining the user to be in an apnea state;
    judging whether the upper airway of the user is clear;
    determining the apnea of the user to be central apnea or obstructive apnea depending on whether the upper airway of the user is clear; and if the apnea of the user is determined to be obstructive apnea adjusting pressure of air supplied by the breathing device;

wherein the step of judging whether the upper airway of the user is clear comprises:
  superimposing an oscillating pressure wave based on the treatment pressure currently supplied by the breathing device to obtain an amount of change in flow and pressure after the oscillating pressure wave is superimposed;
  determining that the upper airway of the user is blocked when the change amount in flow and pressure exceeds a preset change threshold, otherwise, determining that the upper airway of the user is clear;

wherein after the oscillating pressure wave is superimposed, the change amount in flow and pressure is obtained according to an equation as follows:

$$M = \left(\frac{1}{n}\sum_{i-1}^{n} V_i\right) * \left(\frac{1}{n}\sum_{i-1}^{n} p_i\right) / K_2$$

where M is the change amount in flow and pressure,
n is a number of cycles of the oscillating pressure wave superimposed on the treatment pressure,
$V_i$ is a total change amount of the airway flow reference value in each cycle of the oscillating pressure wave,
$p_i$ is a total change amount of an output pressure in each cycle of the oscillating pressure wave, and
$k_2$ is a constant.

2. The method according to claim 1, wherein $V_i$ is obtained according to an equation as follows:

$$V_i = \Sigma_{i-1}^{n}(F - F_i)$$

where F is the airway flow reference value, and
$F_i$ is a minimum value of the airway flow reference value F in each cycle.

3. The method according to claim 1, wherein $p_i$ is obtained according to an equation as follows:

$$p_i = \Sigma_{i-1}^{n}(p - p_{avg})$$

where p is the output power, and
$p_{avg}$ is an average of p for a period of time before the oscillating pressure wave is superimposed.

4. The method according to claim 1, wherein the airway flow reference value is obtained according to an equation as follows:

$$F = \frac{P * N}{K_1}$$

where F is the airway flow reference value,
P is the instantaneous output power of the motor,
N is the instantaneous rotation speed of the motor, and
$K_1$ is a constant.

* * * * *